United States Patent [19]

Caprathe et al.

[11] Patent Number: 4,704,390

[45] Date of Patent: Nov. 3, 1987

[54] PHENYL AND HETEROCYCLIC TETRAHYDROPYRIDYL ALKOXY-BENZHETEROCYCLIC COMPOUNDS AS ANTIPSYCHOTIC AGENTS

[75] Inventors: Bradley W. Caprathe, Redford; Horace A. DeWald, Ann Arbor; Juan C. Jaen, Plymouth; Lawrence D. Wise, Ann Arbor, all of Mich.

[73] Assignee: Warner-Lambert Company, Morris Plains, N.J.

[21] Appl. No.: 924,627

[22] Filed: Nov. 5, 1986

Related U.S. Application Data

[63] Continuation-in-part of Ser. No. 829,036, Feb. 13, 1986, abandoned.

[51] Int. Cl.[4] .................. A61K 31/44; C07D 401/12; C07D 405/12

[52] U.S. Cl. ........................... 514/231; 514/239; 514/255; 514/256; 514/275; 514/307; 514/314; 514/333; 514/337; 514/338; 514/339; 544/105; 544/295; 544/333; 544/357; 544/360; 544/369; 544/370; 544/376; 544/379; 544/405; 546/141; 546/148; 546/177; 546/256; 546/269; 546/271; 546/273

[58] Field of Search .............. 544/105, 333, 405; 546/141, 148, 177, 256, 269, 271, 273; 514/231, 239, 255, 256, 275, 307, 314, 333, 337, 338, 339

[56] References Cited

U.S. PATENT DOCUMENTS 3,929,793 12/1975 Popelak et al. ............... 544/373
4,482,560 11/1984 Banno et al. .................. 514/312

FOREIGN PATENT DOCUMENTS 80322   5/1982 Japan.
145872  9/1982 Japan.
70675   4/1984 Japan.
2071094 9/1981 United Kingdom.

Primary Examiner—Richard L. Raymond
Attorney, Agent, or Firm—Ronald A. Daignault

[57] ABSTRACT

Novel phenyl and heterocyclic tetrahydropyridyl and piperazinyl alkoxy benzheterocyclic compounds are described which have valuable neuroleptic properties by virtue of their dopamine autoreceptor agonist activity. Methods of preparation, pharmaceutical compositions, and methods for treating psychoses, such as schizophrenia, are also described.

13 Claims, No Drawings

PHENYL AND HETEROCYCLIC TETRAHYDROPYRIDYL ALKOXY-BENZHETEROCYCLIC COMPOUNDS AS ANTIPSYCHOTIC AGENTS

This is a continuation-in-part of U.S. application Ser. No. 829,036 filed 2-13-86, now abandoned.

BACKGROUND ON THE INVENTION

The present invention relates to novel phenyl and heterocyclic tetrahydropyridyl and piperazinyl alkoxy benzheterocyclic compounds which have valuable neuroleptic properties by virtue of their dopamine autoreceptor agonist activity.

The invention thus has for its objective the use of these novel compounds as antipsychotic agents for the treatment and management of psychoses, such as schizophrenia.

SUMMARY OF THE INVENTION

Accordingly, the present invention is to a compound of the formula

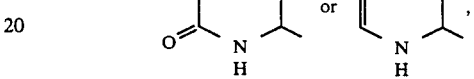

I in which Het is selected from the group consisting of

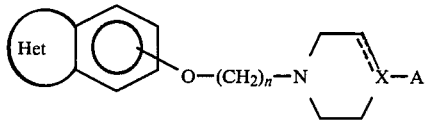

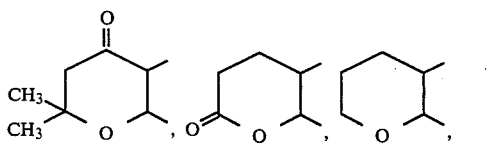

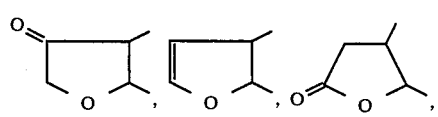

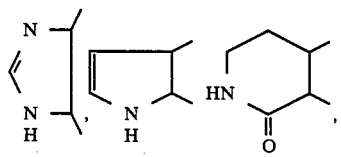

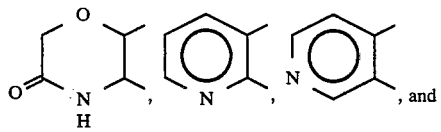

, and

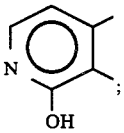

n is an integer from two to five;

represents a single or double bond; X is C or N, and A is phenyl or phenyl substituted by lower alkyl, lower alkoxy, lower thioalkoxy, halogen or trifluoromethyl, 2-, 3- or 4-pyridinyl, or 2-, 3- or 4-pyridinyl substituted by lower alkyl, lower alkoxy or halogen, 2-, 4- or 5-pyrimidinyl or 2-, 4- or 5-pyrimidinyl substituted by lower alkyl, lower alkoxy or halogen, 2-pyrazinyl or 2-pyrazinyl substituted by lower alkyl, lower alkoxy or halogen, 2- or 3-thienyl or 2- or 3-thienyl substituted by lower alkyl or halogen, 2- or 3-furanyl or 2- or 3-furanyl substituted by lower alkyl or halogen, or 2- or 5-thiazolyl or 2- or 5-thiazolyl substituted by lower alkyl or halogen, or a pharmaceutically acceptable acid addition salt thereof, with the proviso that when X is N and Het is

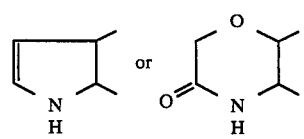

A is not phenyl or substituted phenyl as defined above.

The present invention also relates to a pharmaceutical composition comprising an antipsychotic effective amount of a compound of Formula I or a pharmaceutically acceptable acid addition salt thereof with a pharmaceutically acceptable carrier.

The present invention further relates to a method of treating psychoses, e.g., schizophrenia, in a subject suffering therefrom comprising administering to said subject an effective amount of a compound of the Formula I or a pharmaceutically acceptable acid addition salt thereof in unit dosage form.

DETAILED DESCRIPTION

In the compounds of the Formula I, the term "lower alkyl" is meant to include a straight or branched alkyl group having from one to six carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, chlorine, or bromine.

Lower alkoxy and thioalkoxy are O-alkyl or S-alkyl of from one to six carbon atoms as defined above for "lower alkyl."

A preferred embodiment of the present invention is a compound of Formula I wherein n is the integer three or four.

Another preferred embodiment is a compound of Formula I wherein n is three or four, and A is phenyl or phenyl substituted by methyl, methoxy, thiomethoxy or chloro, 2-, 3- or 4-pyridinyl, 2-, 3- or 4-pyridinyl substituted by methyl, chloro or bromo, 2-, 4- or 5-pyrimidinyl; 2-pyrazinyl or 2-thiazolyl with the same proviso as defined above, i.e., when Het is and X is N, A is not phenyl or substituted phenyl.

Still another preferred embodiment is a compound of Formula I as defined above, wherein n is three or four and A is phenyl, 2-, 3- or 4-pyridyl, 2-, 4- or 5-pyrimidyl, 2-pyrazinyl or 2-thiazolyl.

Particularly preferred embodiments are the following:

1-[3-[6-benzofuranyloxy]propyl]-4-phenylpiperazine;
1-[3-[(3,4-dihydro-2H-1-benzopyran-7-yl)oxy]propyl]-4-phenylpiperazine;
4-[3-(3,6-dihydro-4-phenyl-1(2H-pyridinyl)propoxy]-1H-indole;
4-[4-(3,6-dihydro-4-phenyl-1(2H)-pyridinyl)butoxy]-1H-indole;
5-[4-(3,6-dihydro-4-phenyl-1(2H)-pyridinyl)butoxy]-1H-indole;
6-[3-(3,6-dihydro-4-phenyl-1(2H)-pyridinyl)propoxy]-1H-indole;
6-[3-(4-phenyl-1-piperazinyl)propoxy]-3-(2H)-benzofuranone;
6-[3-[4-(2-pyrimidinyl)-1-piperazinyl]propoxy]-2H-1,4-benzoxazine-3(4H)-one;
6-[3-[4-(2-pyrimidinyl)-1-piperazinyl]propoxy]-1H-indole;
6-[3-(4-phenyl-1-piperazinyl)propoxy]quinoline;
6-[4-[4-(2-pyrimidinyl)-1-piperazinyl]butoxy]quinoline;
6-[4-(3,6-dihydro-4-phenyl-1(2H)-pyridinyl)butoxy]quinoline;
5-[4-[4-(2-pyrimidinyl)-1-piperazinyl]butoxy]quinoline;
5-[3-(3,6-dihydro-4-phenyl-1(2H)-pyridinyl)propoxy]isoquinoline;
5-[3-(4-phenylpiperazinyl)propoxy]-1H-benzimidazole;
1,3-dihydro-5-[3-(4-phenyl-1-piperazinyl)propoxy]-2H-indol-2-one;
5-[3-[4-(2-pyridinyl)-1-piperazinyl]propoxy]isoquinoline;
5-[3-(4-phenyl-1-piperazinyl)propoxy]isoquinoline;
5-[3-[4-(2-pyrimidinyl)-1-piperazinyl]propoxy]isoquinoline;
5-[4-[4-(2-pyrimidinyl)-1-piperazinyl]butoxy]quinoline;
7-[3-[4-(2-pyridinyl)-1-piperazinyl]propoxy]quinoline;
7-[3-(4-phenyl-1-piperazinyl)propoxy]quinoline;
7-[3-[4-(2-pyrimidinyl)-1-piperazinyl]propoxy]quinoline;
5-[3-[4-(2-pyridinyl)-1-piperazinyl]propoxy]-1-isoquinolinol;
3,4-dihydro-5-[3-[4-(2-pyridinyl)-1-piperazinyl]-propoxy-1(2H)-isoquinoline;
7-[3-[4-(2-pyridinyl)-1-piperazinyl]propoxy]isoquinoline;
7-[3-[4-(2-pyrimidinyl)-1-piperazinyl]propoxy]isoquinoline;
or a pharmaceutically acceptable acid addition salt thereof.

The compounds of the invention form pharmaceutically acceptable acid addition salts with organic and inorganic acids. Examples of suitable acids for salt formulation are hydrochloric, sulfuric, phosphoric, acetic, citric, oxalic, malonic, salicyclic, malic, fumaric, succinic, ascorbic, maleic, methanesulfonic, and the like. The salts are prepared by contacting the free base form with a sufficient amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The compounds of the present invention and of the formula I may be prepared by first reacting a hydroxy benzheterocyclic compound of the formula

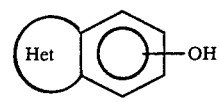

II wherein Het is as defined above, with a compound of the formula

$Z-(CH_2)_n-Y$       III where n is an integer from two to five; Z and Y are the same or different and are a leaving group such as halogen or a sulfonyloxy group, for example, methanesulfonyloxy or p-toluenesulfonyloxy; and secondly, reacting the resulting product of the Formula IV

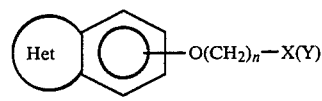

IV with an amine of the formula

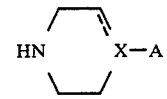

V wherein X and A are as defined previously, and if desired, converting the resulting free base by known methods to a pharmaceutically acceptable acid addition salt.

The reaction of the compound of Formula II with a compound of Formula III is carried out in an inert solvent, preferably a polar solvent such as a ketone, for example, acetone or methyl isobutyl ketone, in the presence of an acid scavenger, such as, for example, sodium or preferably, potassium carbonate in anhydrous form, at the reflux temperature of the solvent.

The intermediate product of Formula IV is then reacted with the appropriate amine in a polar aprotic solvent such as, for example, dimethylformamide and in the presence of a neutralizing agent such as, for example, sodium bicarbonate. The reaction is carried out at elevated temperatures, e.g., from about 50° to 150° C.

An alternate method for the preparation of a compound of Formula I is to first prepare a compound of the formula

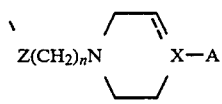

VI wherein Z, X, and A are as defined above, according to a method described in *Ind. J. Chem* 435 (1982), and react said compound of Formula VI directly with a benzoheterocyclic compound of Formula II. This reaction is also best carried out at elevated temperatures, e.g., 50°–150° C., in a solvent such as dimethylformamide and in the presence of an acid neutralizing agent such as sodium bicarbonate.

The appropriate benzheterocyclic derivatives, compounds of Formula II, and amine derivatives, compounds of Formula V, are available commercially or may be prepared by well-known methods.

The compounds of the present invention are new chemical substances which are useful as pharmaceutical agents for the treatment of psychoses such as, for example, schizophrenia. The antipsychotic activity of representative compounds of the invention was established by the inhibition of locomotor activity-screen fall-off test described below:

ANIMALS: Nine unfasted Swiss-Webster male mice (Buckberg Labs) weighing 20–30 g are equally divided into three groups for each drug dose to be tested. That is, data for each dose level was generated by three separate groups of three mice each.

DRUGS: A minimum of three dose levels (10, 30, and 100 mg/kg) are tested for each drug. Treatments are administered intraperitoneally one hour prior to testing. All dosages are calculated as parent compound. Compounds are dissolved or suspended in 0.2% methocel. Control animals are injected with methocel.

TESTING: A two-part testing procedure is started one hour postinjection. First, the screen test is performed (see Pharmac Biochem Behav 6, 351–353, 1977). Briefly, this test consists of placing mice on individual wire screens which are then rotated 180° at the start of a 60-second observation period. The number of mice falling off the inverted screen is recorded.

Immediately following the screen test, the final phase of testing is initiated by placing each group of three mice in one actophotometer (*Life Sciences*, 22, 1067–1076, 1978). The actophotometer consists of a cylindrical chamber whose center is occupied by another cylinder which contains the illumination for six photocells located on the perimeter of the chamber. Six light-beam interruptions equal one count. Locomotor activity is recorded by computer at ten-minute intervals for 60 minutes.

DATA: The data obtained from the screen test are expressed as percent of mice falling off the screen. Data derived from locomotor activity of drug-treated mice are compared to the activity of vehicle-treated animals and are expressed as percent inhibition of spontaneous locomotion. All percentages reported for inhibition of locomotion are based upon data accumulated for one hour. Both phases of testing are graded: A=60–100%; C=31–59%; and N=0–30%. An overall dose rating is obtained by the following criteria.

| Inhibition of | Screen Test | | Dose |
|---|---|---|---|
| Locomotion rating with Failure Rating | = | | Rating |
| A | — | N or C = | A |
| A | — | A = | C |
| C | — | N or C = | C |
| | All other combinations | = | N |

Compounds which exhibit an overall dose rating of A at a dose of 100 milligrams/kilogram or less are considered active. Utilizing this procedure, an overall dose rating of A was obtained for the noted compounds at the indicated dose, $ED_{50}s$, as reported in Table 1.

The antipsychotic activity of representative compounds of the invention was also established by the [$^3$H] haloperidol binding assay method which is described in *Mol. Pharmacol.* 12, 800 (1976) and reports excellent correlation between the amount of binding and clinical potency.

[$^3$H] Haloperidol Binding Assay

The relative affinities of compounds for dopamine receptors were evaluated on the basis of their ability to displace [$^3$H]-haloperidol from striatal membranes prepared from Long-Evans hooded rats. Rats were decapitated; the brains were removed, and the corpus striata were dissected. The corpus striata were homogenized in 40 volumes of 50 nM Tris buffer (pH 7.6) and centrifuged. Pellets were rehomogenized in 50 volumes of the same buffer and used for the binding assay. Incubations were carried out in 10 ml of 50 nM Tris-HCl buffer (pH 7.6) containing 2 mg/ml of original wet tissue weight of homogenate, 100 μl of test agent or solvent, and 0.6 nM of [$^3$H]-haloperidol. Nonspecific binding was determined in the presence of 0.1 μM (+)-butaclamol. Samples were incubated in reciprocating water bath at 25° C. for 40 minutes. Incubation was terminated by rapid filtration under reduced pressure through glass fiber filters (Whatman GF/B). The filters were rinsed three times with 10 ml of Tris-HCl buffer. The filters were placed in 10 ml of scintillation cocktail (Beckman Ready-Solv HP) and shaken for one hour. Radioactivity retained on the filter was determined by liquid scintillation spectrophotometry. $IC_{50}s$ when determined were calculated from a nonlinear computer curve, fit on the data from four or concentrations, each done in triplicate.

$IC_{50}s$ for representative compounds of the present invention are also reported in Table 1.

TABLE 1

| Compound Example No. | Inhibition of Locomotor Activity $ED_{50}$ mg/kg | $^3$H—Haloperidol Binding IC50, nM |
|---|---|---|
| 1 | 5.9 | 300 |
| 2A | 4.8 | <100 |
| 2B | 3.7 | 100 |
| 2C | 3.5 | <100 |
| 2D | 2.7 | 70 |
| 2E | 1.0 | 1,000 |
| 2F | 2.5 | 40 |
| 2G | 1.4 | 50 |
| 2H | 0.5 | 10 |
| 2I | 2.8 | 100 |
| 2J | 3.2 | 200 |
| 2K | 0.5 | 90 |
| 2L | 0.9 | 50 |
| 2M | 1.1 | 17 |
| 2N | 7.7 | 180 |
| 2O | 0.18 | 33 |
| 2P | 3.0 | 645 |
| 2Q | 0.29 | 206 |
| 2R | 19.5 | 947 |
| 2S | 7.7 | 184 |
| 2T | 0.17 | 230 |
| 2U | 0.10 | 50 |
| 2V | 1.0 | 900 |
| 2W | 6.1 | 651 |
| 2X | 4.4 | 431 |
| 3 | 4.9 | 120 |
| 4 | 0.4 | 160 |
| 5 | 8.8 | 500 |

The compounds of the present invention can be prepared and administered in a wide variety of oral and parenteral dosage forms. It will be obvious to those skilled in the art that the following dosage forms may comprise as the active component, either a compound of Formula I, a corresponding pharmaceutically acceptable salt of a compound of Formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low-melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as antipsychotic agents, the compounds utilized in the pharmaceutical method of this invention are administered at the initial dosage of about 0.1 mg to about 10 mg per kilogram daily. A daily dose range of about 1.0 mg to about 10 mg per kilogram is preferred.

The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventor's preferred methods for preparing the compounds of the invention.

EXAMPLE 1

2,3-Dihydro-2,2-dimethyl-7-(3-(4-phenyl)-1-piperizinyl)propoxy-4H-benzopyran-4-one Procedure A A mixture of 7 g (0.026 mol) of 7-(3-chloropropoxy)-2,3-dihydro-2,2-dimethyl-4H-benzopyran-4-one and 4.5 g (0.019 mol) of N-phenylpiperazine in 100 ml of DMF containing 5 g of sodium bicarbonate was stirred at 80°–90° C. for 18 hours. The mixture was filtered and the filtrate was evaporated in vacuo. The residue was dissolved in $CH_2Cl_2$, washed with $H_2O$, dried over $MgSO_4$ and the solvent evaporated in vacuo. The oil was dissolved in 40 ml of 2-propanol and treated with excess 20% isopropanolic hydrogen chloride to give 7.3 g (64%) mp 220°–222° C. of the product as the dihydrochloride salt.

Procedure B

A mixture of 5.8 g (0.03 mol) of 2,3-dihydro-2,2-dimethyl-7-hydroxy-4H-benzopyran-4-one, 5 g anhydrous potassium carbonate, and 7 g (0.03 mole) N'-(3-chloropropoxy) N-phenylpiperazine in 100 ml of DMF was stirred at 80°–90° C. for 20 hours. The mixture was filtered and the filtrate evaporated in vacuo. The residue, dissolved in $CH_2Cl_2$, was washed with 1N NaOH, water, dried ($MgSO_4$) and the solvent evaporated in vacuo to give 11 g of crude product. This material was dissolved in 40 ml of 2-propanol and treated with hydrogen chloride as in Procedure A to give the same dihydrochloride, mp 220°–2° C., yield: (60%).

EXAMPLE 2

Using Procedure A of Example 1, the following compounds were prepared:

A. 7-[3-[3,6-dihydro-4-phenyl-1(2H)-pyridinyl)propoxy]-2,3-dihydro-2,2-dimethyl-4H-benzopyran-4-one hydrochloride, mp 214°–16° C. from propanol;

B. 6-[3-(4-phenyl-1-piperazinyl)propoxy]-3-(2H)-benzofuranone, mp 129°–31° C. from ethyl acetate;

C. 6-[3-(3,6-dihydro-4-phenyl-1-(2H)-pyridinyl)propoxy]-3(2H)-benzofuranone, mp 112°–14° C. from diethyl ether;

D. 1-[3-[(3,4-dihydro-2H-1-benzopyran-7-yl)oxy]-propyl]-4-phenylpiperazine, mp 84°–6° C. from ethyl acetate;

E. 6-[3-[4-(2-pyrimidinyl)-1-piperazinyl]propoxy]-2H-1,4-benzoxazine-3(4H)-one, mp 143°–5° C.;

F. 4-[3-(3,6-dihydro-4-phenyl-1(2H)-pyridinyl)propoxy]-1H-indole, mp 147°–50° C.;

G. 4-[4-(3,6-dihydro-4-phenyl-1(2H)-pyridinyl)butoxy]-1H-indole, mp 130°–2° C.;

H. 5-[4-(3,6-dihydro-4-phenyl-1(2H)-pyridinyl)butoxy]-1H-indole, mp 117°–9° C.;
I. 6-[3-(3,6-dihydro-4-phenyl-1(2H)-pyridinyl)propoxy]-1H-indole monohydrate, mp 198°–202° C.;
J. 6-[3-[4-(2-pyrimidinyl)-1-piperazinyl]propoxy]-1H-indole, mp 150°–1° C.;
K. 6-[3-(4-phenyl-1-piperazinyl)propoxy]-quinoline monohydrate, mp 114°–6° C.;
L. 6-[4-[4-(2-pyrimidinyl)-1-piperazinyl]butoxy]quinoline trihydrochloride hemihydrate, mp 240°–3° C.;
M. 6-[4-(3,6-dihydro-4-phenyl-1(2H)-pyridinyl)butoxy]-quinoline 1.8 hydrochloride monohydrate, mp 180°–92° C.;
N. 5-[4-[4-(2-pyrimidinyl)-1-piperazinyl]butoxy]quinoline 1.9 hydrate, mp 107°–110° C.;
O. 5-[3-(3,6-dihydro-4-phenyl-1(2H)-pyridinyl)propoxy]isoquinoline dihydrochloride, mp 230°–2° C.;
P. 5-[3-[4-(2-pyridinyl)-1-piperazinyl]propoxy]isoquinoline trihydrochloride, mp 260°–3° C. (dec);
Q. 5-[3-(4-phenyl-1-piperazinyl)propoxy]isoquinoline, hydrochloride, mp 125° C. (dec);
R. 5-[3-[4-(2-pyrimidinyl)-1-piperazinyl]propoxy]isoquinoline, hydrochloride, mp 263°–6° C. (dec);
S. 5-[4-[4-(2-pyrimidinyl)-1-piperazinyl]butoxy]quinoline, dihydrate, mp 107°–110° C.;
T. 7-[3-[4-(2-pyridinyl)-1-piperazinyl]propoxy]quinoline trihydrochloride, monohydrate, mp 257°–9° C. (dec);
U. 7-[3-(4-phenyl-1-piperazinyl)propoxy]quinoline, mp 100°–2° C.;
V. 7-[3-[4-(2-pyrimidinyl)-1-piperazinyl]propoxy]-quinoline, monohydrate, mp 223°–5° C.;
W. 5-[3-[4-(2-pyridinyl)-1-piperazinyl]propoxy]-1-isoquinolinol, mp 153°–5° C.;
X. 3,4-dihydro-5-[3-[4-(2-pyridinyl)-1-piperazinyl]propoxy]-1(2H)-isoquinoline, dihydrochloride; mp 235°–240° C.;
Y. 7-[3-[4-(2-pyridinyl)-1-piperazinyl]propoxy]isoquinoline, dihydrate, mp 212°–6° C.; and
Z. 7-[3-[4-(2-pyrimidinyl)-1-piperazinyl]propoxy]isoquinoline, trihydrate, mp 228°–231° C.

EXAMPLE 3

5-[3-(4-Phenylpiperazinyl)propyloxy]-1H-benzimidazole trihydrochloride trihydrate Sodium metal (0.37 g; 16 mmole) was dissolved in 10 ml of absolute ethanol. To this solution was added 2.01 g (15 mmole) of 5-hydroxy-1H-benzimidazole while cooling in an ice bath. The resulting solution was stirred at 0° C. for 30 minutes. A solution of 3.57 g (15 mmole) of 1-(3-chloropropoxy)-4-phenylpiperazine in 2 ml ethanol was then added and stirring was continued at room temperature for 16 hours. The solvent was evaporated in vacuo and the residue was purified by medium pressure liquid chromatography (MPLC) on Silica Gel, using ethyl acetate as the eluent. The 1.5 g (30%) of material obtained was dissolved in 10 ml of isopropanol and treated with an excess of saturated solution of hydrogen chloride in isopropanol. Upon standing, a crystalline material appeared which was filtered, washed with ether, and air-dried. A sticky white solid was obtained which was characterized as 5-[3-(4-phenylpiperazinyl)propyloxy]-1H-benzimidazole trihydrochloride trihydrate.

EXAMPLE 4

Using the procedure of Example 3, 1,3-dihydro-5-[3-(4-phenyl-1-piperazinyl)propoxy]-2H-indole-2-one was prepared, mp 166°–78° C.

EXAMPLE 5

1-[3-[6-Benzofuranyloxy]propyl]-4-phenylpiperazine

6-[3-(4-phenyl-1-piperazinyl)propoxy]-3-(2H)-benzofuranone, 9 g, 0.25 mole, in 125 ml dioxane was treated with 3 g of sodium borohydride at reflux for two hours. The mixture was evaporated then partitioned in water and ethyl acetate. The ethyl acetate layer was evaporated to give the resulting alcohol, mp 80°–5° C. (7.5 g).

The above intermediate (4 g) was stirred in 10% hydrochloric acid (30 ml) and 10 ml trifluoroacetic for two hours at room temperature and then made basic. The reaction mixture was extracted with methylene chloride and evaporated to give 4 g of oil. The crude product was converted to 3.6 g (85%) of the dihydrochloride salt, mp 187°–189° C. with isopropanolic HCl.

PREPARATION OF STARTING MATERIALS

EXAMPLE A 2,3-Dihydro-2,2-dimethyl-7-Hydroxy-benzopyran-4-one 2,3-Dihydro-2,2-dimethyl-7-methoxy-benzopyran-4-one 20 g (0.1 mole), obtained as described in *Chem. Pharm. Bull.* 25, 2788 (1977) was refluxed for one hour in 150 g of pyridine hydrochloride then poured into 1 liter of water. The solids were collected on a filter and recrystallized from isopropanol to give 11 g (60%) of product, mp 164°–7° C.

2,3-Dihydro-2,2-dimethyl-7-(3-chloropropoxy)-4H-1-benzopyran-4-one

The above product was refluxed for 16 hours with 11 g of 3-bromo-1-chloropropane, 10 g anhydrous potassium carbonate in acetone. The mixture was filtered and concentrated. The residue was percolated over silica gel in ethyl acetate to give 14 g of the product (70%) isolated as an oil.

EXAMPLE B 6-(3-Chloropropoxy)-3-(2H)-benzofuranone

6-Hydroxy-3-(2H)-benzofuranone obtained as described in *J. Chem. Soc.* 1950, 3211, was refluxed with 3-bromo-1-chloropropane and anhydrous potassium carbonate in acetone as described in Example A to give the desired product, mp 78°–81° C. from diethyl ether/petroleum ether.

EXAMPLE C 7-(3-chloropropoxy)-benzopyran

7-Hydroxybenzopyran-4-one obtained as described in *J. Chem. Soc.*, 1958, 1191, was hydrogenated with Palladium on charcoal catalyst to give the corresponding 7-hydroxybenzopyran.

Treatment of the benzopyran with 3-bromo-1-chloropropane and potassium carbonate in acetone as described previously gave as an oil 7-(3-chloropropoxy)-benzopyran.

EXAMPLE D

7-(3-chloropropoxy)-2H-1,4-benzoxazin-3(4H)-one

7-Hydroxy-2H-1,4-benzoxazin-3(4H)-one was treated with 3-bromo-1-chloro-propane and sodium metal in ethyleneglycol monoethyl ether to give the desired product in 65% yield, mp 95° C.

EXAMPLE E

6-Hydroxyindole

A solution of 5.0 g (20.6 mmole) of 4-benzyloxy-2-nitro toluene and 5.0 g (41.9 mmole) of N,N-dimethylformamide dimethyl acetal in 75 ml DMF was refluxed under argon for 12 hours. The mixture was cooled and a solution of 2.41 g of semicarbazide hydrochloride in 50 ml water containing 1.9 ml of concentrated HCl was added. A precipitate immediately formed. After cooling further, the precipitate was filtered and washed with cold water, and ether. The solid was then dried in vacuo. Yield=5.0 g (74.6%).

The semicarbazone obtained above was reduced catalytically using 10% palladium on carbon in ethanol to yield a mixture of 6-hydroxyindole 38% yield, mp 124°-6° C., and 3-amino-4-methylphenol which were separated by column chromatography.

EXAMPLE F

5-Hydroxy-1H-benzimidazole

Twenty grams (0.114 mole) of 4-methoxy-1,2-phenylenediamine hydrochloride was refluxed with 30 ml of 88% formic acid, 15 ml of concentrated HCl and 90 ml of water for eight hours. The solvent was then removed in vacuo and the residue was treated with 100 ml of concentrated NH$_4$OH, extracted with dichloromethane (2×200 ml), dried over MgSO$_4$ and concentrated to leave a thick oil which was converted to its HCl salt, mp 212°-5° C. (12.8 g, 60%). This compound (12.0 g, 65 mmole) was refluxed with 125 ml of concentrated HBr, under argon, for three hours. After evaporation in vacuo, the residue was dissolved in water, neutralized with solid NaHCO$_3$. The product deposited was recrystallized from water, yielding 7.7 g (88%) of 5-hydroxy-1H-benzimidazole, mp 216°-8° C.

What is claimed is:

1. A compound of the formula

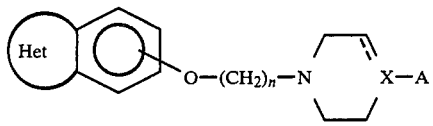

I in which Het is selected from the group consisting of

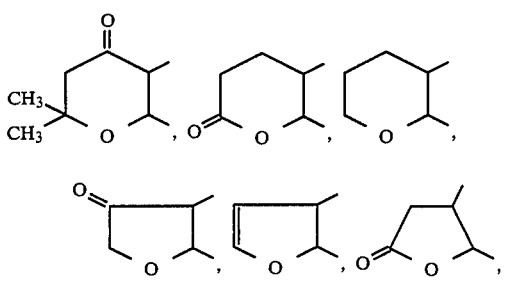

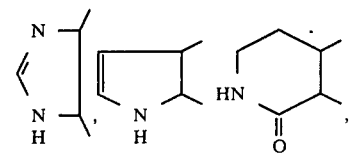

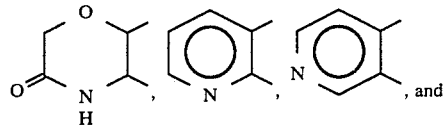

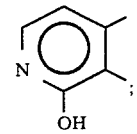

n is an integer from two to five;

== represents a double bond; X is C, and A is phenyl or phenyl substituted by lower alkyl, lower alkoxy, lower thioalkoxy, halogen or trifluoromethyl; 2-, 3- or 4-pyridinyl or 2-, 3- or 4-pyridinyl substituted by lower alkyl, lower alkoxy or halogen; 2-, 4- or 5-pyrimidinyl, or 2-, 4- or 5-pyrimidinyl substituted by lower alkyl, lower alkoxy or halogen; 2-pyrazinyl or 2-pyrazinyl substituted by lower alkyl, lower alkoxy or halogen; 2- or 3-thienyl or 2- or 3-thienyl substituted by lower alkyl or halogen; 2- or 3-furanyl or 2- or 3-furanyl substituted by lower alkyl or halogen, or 2- or 5-thiazolyl or 2- or 5-thiazolyl substituted by lower alkyl or halogen, or a pharmaceutically acceptable acid addition salt thereof, with the exclusion of the compound wherein X is N, Het is

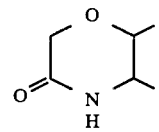

or

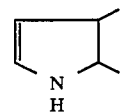

and A is phenyl or substituted phenyl.

2. A compound according to claim 1, wherein n is the integer three or four.

3. A compound according to claim 2, wherein A is phenyl or phenyl substituted by methyl, methoxy, thiomethoxy or chloro; 2-, 3- or 4-pyridinyl, 2-, 3- or 4-pyridinyl substituted by methyl, chloro or bromo; 2-, 4- or 5-pyrimidinyl; 2-pyrazinyl, or 2- or 5-thiazolyl.

4. A compound according to claim 3, wherein A is phenyl, 2-, 3- or 4-pyridinyl, 2-, 4- or 5-pyrimidinyl, 2-pyrazinyl, or 2- or 5-thiazolyl.

5. A compound according to claim 4 and being 7-[3-[3,6-dihydro-4-phenyl]-1(2H)-pyridinyl)-propoxy]-2,3-dihydro-2,2-dimethyl-4H-benzopyran-4-one.

6. A compound according to claim 4 and being 4-[3-(3,6-dihydro-4-phenyl-1(2H)-pyridinyl)propoxy]-1H-indole.

7. A compound according to claim 4 and being 4-[4-(3,6-dihydro-4-phenyl-1(2H)-pyridinyl)butoxy]-1H-indole.

8. A compound according to claim 4 and being 5-[4-(3,6-dihydro-4-phenyl-1(2H)-pyridinyl)butoxy]-1H-indole.

9. A compound according to claim 4 and being 6-[3-(3,6-dihydro-4-phenyl-1(2H)-pyridinyl)propoxy]-1H-indole.

10. A compound according to claim 4 and being 6-[4-(3,6-dihydro-4-phenyl-1(2H)-pyridinyl)butoxy]quinoline.

11. A compound according to claim 4 and being 5-[3-(3,6-dihydro-4-phenyl-1(2H)-pyridinyl)propoxy]isoquinoline.

12. A pharmaceutical composition comprising an antipsychotic effective amount of a compound as claimed in claim 1 or a pharmaceutically acceptable acid addition salt thereof with a pharmaceutically acceptable carrier.

13. A method of treating psychosis in a subject suffering therefrom comprising administering to said subject 12 a pharmaceutical composition according to claim 8 in unit dosage form.

* * * * *

UNITED STATES PATENT AND TRADEMARK OFFICE
CERTIFICATE OF CORRECTION

PATENT NO. : 4,704,390

DATED : November 3, 1987

INVENTOR(S) : Bradley W. Caprathe, et al

It is certified that error appears in the above-identified patent and that said Letters Patent is hereby corrected as shown below:

Column 14, line 14, delete "12".

Column 14, line 14, delete "claim 8" and substitute
--claim 12--.

Signed and Sealed this

First Day of November, 1988

Attest:

DONALD J. QUIGG

Attesting Officer     Commissioner of Patents and Trademarks